(12) United States Patent
Cabiac et al.

(10) Patent No.: US 8,754,247 B2
(45) Date of Patent: Jun. 17, 2014

(54) CATALYST COMPRISING AT LEAST ONE IZM-2 ZEOLITE, AND ITS USE IN THE TRANSFORMATION OF HYDROCARBON FEEDS

(75) Inventors: Amandine Cabiac, Lyons (FR); Nicolas Cadran, Oullins (FR); Emmanuelle Guillon, Vourles (FR); Vincent Lecocq, Brignais (FO); Sylvie Maury, Charly (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 797 days.

(21) Appl. No.: 13/057,846

(22) PCT Filed: Jul. 21, 2009

(86) PCT No.: PCT/FR2009/000898
§ 371 (c)(1),
(2), (4) Date: Sep. 14, 2011

(87) PCT Pub. No.: WO2010/015732
PCT Pub. Date: Feb. 11, 2010

(65) Prior Publication Data
US 2012/0022279 A1 Jan. 26, 2012

(30) Foreign Application Priority Data
Aug. 8, 2008 (FR) .................................... 08 04561

(51) Int. Cl.
| | | |
|---|---|---|
| C09F 7/00 | (2006.01) | |
| C11C 3/00 | (2006.01) | |
| B01J 29/04 | (2006.01) | |
| B01J 29/06 | (2006.01) | |
| C07C 2/68 | (2006.01) | |

(52) U.S. Cl.
USPC .................. 554/167; 554/26; 502/60; 502/63; 502/70; 585/468; 585/470; 585/533; 585/639

(58) Field of Classification Search
USPC .......... 502/60, 64, 73; 554/26, 167; 585/468, 585/470, 533, 639
See application file for complete search history.

(56) References Cited

U.S. PATENT DOCUMENTS

| | | |
|---|---|---|
| 4,539,193 A | 9/1985 | Valyocsik |
| 2006/0210472 A1 | 9/2006 | Hastoy et al. |
| 2009/0192031 A1 | 7/2009 | Guillon et al. |
| 2010/0272624 A1 | 10/2010 | Fecant et al. |

FOREIGN PATENT DOCUMENTS

| | | | |
|---|---|---|---|
| EP | 1 702 888 A | 9/2006 | |
| EP | 1 953 118 A | 8/2008 | |
| EP | 1953118 A1 * | 8/2008 | ............. C01B 37/02 |
| WO | WO 2009/004131 A | 1/2009 | |

OTHER PUBLICATIONS

International Search Report of PCT/FR2009/000898 Date of Completion Jan. 5, 2010, Date of Mailing Jan. 13, 2010, 2 pages.

* cited by examiner

Primary Examiner — Deborah D Carr
(74) Attorney, Agent, or Firm — Millen, White, Zelano & Branigan, P.C.

(57) ABSTRACT

A catalyst is described which comprises at least one IZM-2 zeolite and at least one matrix, said zeolite having a chemical composition expressed as the anhydrous base in terms of moles of oxides by the following general formula: $XO_2$: $aY_2O_3$: $bM_nO$, in which X represents at least one tetravalent element, Y represents at least one trivalent element and M is at least one alkali metal and/or alkaline-earth metal, a and b respectively representing the number of moles of $Y_2O_3$ and $M_nO$; and a is in the range 0.001 to 0.5, b is in the range 0 to 1 and n is in the range 1 to 2. Said catalyst is used in various processes for the transformation of hydrocarbon feeds.

20 Claims, No Drawings

CATALYST COMPRISING AT LEAST ONE IZM-2 ZEOLITE, AND ITS USE IN THE TRANSFORMATION OF HYDROCARBON FEEDS

The present invention relates to the field of zeolitic catalysts and to their use in various processes for the transformation of hydrocarbon feeds. More precisely, the present invention relates to a catalyst comprising at least one IZM-2 zeolite and at least one matrix.

PRIOR ART

Microporous crystalline materials such as zeolites or silicoaluminophosphates are solids which are widely used in the oil industry as catalysts, catalyst supports, adsorbants or separation agents. Although many microporous crystalline structures have been discovered, the refining and petrochemicals industry is constantly seeking out novel zeolitic structures which have particular properties for applications such as purification or separation of gases, or the conversion of carbonaceous or other species. The properties of a zeolitic catalyst are greatly dependent on the porous structure of the zeolite it contains, on its stability and on its acidity.

SUMMARY AND ADVANTAGE OF THE INVENTION

The present invention concerns a catalyst comprising at least one IZM-2 zeolite and at least one matrix, said zeolite having an X ray diffraction diagram including at least the peaks recorded in Table 1 and having a chemical composition expressed as the anhydrous base in terms of moles of oxides by the following general formula: $XO_2$: $aY_2O_3$: $bM_nO$, in which X represents at least one tetravalent element, Y represents at least one trivalent element and M is at least one alkali metal and/or alkaline-earth metal, a and b respectively representing the number of moles of $Y_2O_3$ and $M_nO$; and a is in the range 0.001 to 0.5, b is in the range 0 to 1 and n is in the range 1 to 2.

Said catalyst in accordance with the invention is advantageously used to carry out various processes for the transformation of hydrocarbon feeds. In particular, said catalyst of the invention produces interesting catalytic performances when it is used in the transformation of hydrocarbons, alcohols or triglycerides.

DESCRIPTION OF THE INVENTION

The present invention concerns a catalyst comprising at least one IZM-2 zeolite and at least one matrix, said zeolite having an X ray diffraction diagram including at least the peaks recorded in Table 1 below:

TABLE 1

Mean values of $d_{hkl}$ and relative intensities measured on an X ray diffraction diagram of the calcined IZM-2 zeolite

| 2 theta (°) | $d_{hkl}$ (Å) | $I_{rel}$ |
|---|---|---|
| 5.07 | 17.43 | Vw |
| 7.36 | 12.01 | Vs |
| 7.67 | 11.52 | Vs |
| 8.78 | 10.07 | S |
| 10.02 | 8.82 | Vw |
| 12.13 | 7.29 | Vw |
| 14.76 | 6.00 | Vw |
| 15.31 | 5.78 | Vw |
| 15.62 | 5.67 | Vw |
| 16.03 | 5.52 | Vw |
| 17.60 | 5.03 | Vw |
| 18.22 | 4.87 | Vw |
| 19.01 | 4.66 | Vw |
| 19.52 | 4.54 | Vw |
| 21.29 | 4.17 | M |
| 22.44 | 3.96 | W |
| 23.10 | 3.85 | Mw |
| 23.57 | 3.77 | W |
| 24.65 | 3.61 | Vw |
| 26.78 | 3.33 | W |
| 29.33 | 3.04 | Vw |
| 33.06 | 2.71 | Vw |
| 36.82 | 2.44 | Vw |
| 44.54 | 2.03 | Vw | in which: Vs = very strong; S = strong; M = medium; Mw = medium weak; W = weak; Vw = very weak, and having a chemical composition expressed as the anhydrous base in terms of moles of oxides by the following general formula: $XO_2$: $aY_2O_3$: $bM_nO$, in which X represents at least one tetravalent element, Y represents at least one trivalent element and M is at least one alkali metal and/or alkaline-earth metal, a and b respectively representing the number of moles of $Y_2O_3$ and $M_nO$; and a is in the range 0.001 to 0.5, b is in the range 0 to 1 and n is in the range 1 to 2.

The diffraction diagram the data for which is given in Table 1 is obtained by radiocrystallographic analysis using a diffractometer employing the conventional powder technique with the $K_{\alpha 1}$ peak of copper ($\lambda$=1.5406 Å). From the position of the diffraction peaks represented by the angle 2θ, the characteristic interplanar spacings $\Delta d_{hkl}$ of the sample are calculated using the Bragg relationship. The error in the measurement $\Delta(d_{hkl})$ of $d_{hkl}$ is calculated by the Bragg relationship as a function of the absolute error $\Delta(2\theta)$ in the measurement of 2θ. An absolute error $\Delta(2\theta)$ of ±0.02° is customarily acceptable. The relative intensity $I_{rel}$ in each value of $d_{hkl}$ is measured from the height of the corresponding diffraction peak. The X ray diffraction diagram of the IZM-2 zeolite present in the catalyst of the invention comprises at least the peaks at the values of $d_{hkl}$ given in Table 1. In the $d_{hkl}$ column, the mean values of the interplanar spacings are shown in Angstroms (Å). Each of these values must be supplemented with an error measurement $\Delta(d_{hkl})$ in the range ±0.6 Å to ±0.01 Å.

The IZM-2 zeolite present in the catalyst of the invention has a chemical composition expressed as the anhydrous base in terms of moles of oxides defined by the following general formula: $XO_2$: $aY_2O_3$: $bM_nO$, in which X represents at least one tetravalent element, Y represents at least one trivalent element and M is at least one alkali metal and/or alkaline-earth metal. In said formula given hereinabove, a represents the number of moles of $Y_2O_3$ and a is in the range 0.001 to 0.5, preferably in the range 0.001 to 0.05, more preferably in the range 0.001 to 0.02; b represents the number of moles of $M_nO$ and is in the range 0 to 1, preferably in the range 0 to 0.5, more preferably in the range 0.005 to 0.5; n is in the range 1 to 2, preferably, n is equal to 1 or n is equal to 2.

In accordance with the invention, X is preferably selected from silicon, germanium, titanium and a mixture of at least two of these tetravalent elements; more preferably, X is silicon and Y is preferably selected from aluminium, boron, iron, indium and gallium; more preferably, Y is aluminium. In the IZM-2 zeolite present in the catalyst of the invention, X is preferably silicon and Y is preferably aluminium. M is preferably selected from lithium, sodium, potassium, caesium, rubidium, calcium, magnesium and barium and a mixture of at least two of said metals; highly preferably, M is sodium and/or caesium.

The IZM-2 zeolite present in the catalyst of the invention and containing X and Y atoms as defined above, preferably aluminium atoms and silicon atoms, has an overall X/Y atomic ratio, preferably an overall Si/Al atomic ratio, in the range 5 to 100, preferably in the range 10 to 50 and more preferably in the range 10 to 35. The IZM-2 zeolite present in the catalyst of the invention may also be dealuminated. Highly advantageously, the IZM-2 zeolite present in the catalyst of the invention is in the protonated form (hydrogen form, $H^+$), in which the proportion of cations other than $H^+$ is less than 30% of the total number of cations, preferably less than 20% and more preferably less than 5% with respect to the total number of cations on the zeolite. In accordance with the invention, when the IZM-2 zeolite is in the protonated form, coefficient b is zero in the formula: $XO_2: aY_2O_3: bM_nO$ given above. However, for applications such as the manufacture of alcoholic esters from triglycerides and alcohols as will be described below, the IZM-2 zeolite present in the catalyst of the invention is in the basic form, the proportion of alkali and/or alkaline-earth cations other than $H^+$ being much more than 30% of the total number of cations, preferably more than 70% and highly preferably more than 80% of the total number of cations. When said IZM-2 zeolite present in the catalyst of the invention is in the basic form, it is preferably exchanged with caesium.

The matrix present in the catalyst of the invention is a porous mineral matrix, generally amorphous. It is selected from elements from the group formed by aluminas, silicas, magnesia, amorphous silica-aluminas, natural clays (kaolin, bentonite, sepiolite, attapulgite), titanium oxide, boron oxide, zirconia, phosphates of aluminium, phosphates of titanium, phosphates of zirconium, charcoal and mixtures thereof. Preferably, a matrix containing alumina is used, particularly in all of the forms known to the skilled person, more preferably gamma alumina. Further, mixtures of alumina and silica, mixtures of alumina and silica-alumina may advantageously be used.

The catalyst of the invention advantageously comprises at least one additional metal selected from metals from groups IIIb, IVa and IVb; said catalyst comprises a metal selected from metals from groups IIIb, IVa and IVb or several metals as a mixture selected from metals from groups IIIb, IVa and IVb, for example a metal from group IIIb and a metal from group IVb. Preferred metals from group IIIb are lanthanum and cerium. Preferred metals from group IVa are tin and germanium. Preferred metals from group IVb are titanium and zirconium.

The catalyst of the invention is free of any sulphide phase. More particularly, said catalyst of the invention contains:
- 1% to 90%, preferably 3% to 80% and more preferably 4% to 60% by weight of at least said IZM-2 zeolite;
- 10% to 99%, preferably 20% to 97% and more preferably 40% to 96% by weight of at least one matrix;
- optionally, 0.01% to 2%, preferably 0.05% to 1% by weight of at least one additional metal selected from metals from groups IIIb, IVa and IVb.

The catalyst of the invention is preferably in the form of beads or extrudates. It has mechanical properties such that the value for the bed crush strength, determined using the Shell method (SMS 1471-74), is preferably more than 0.7 MPa.

The present invention also pertains to the preparation of the catalyst of the invention. Preparation of the catalyst of the invention commences with preparation of the IZM-2 zeolite.

Said IZM-2 zeolite present in the catalyst of the invention is prepared using a process in which the following are reacted: an aqueous mixture comprising at least one source of at least one oxide $XO_2$, at least one source of at least one oxide $Y_2O_3$, at least one source of at least one alkali and/or alkaline-earth metal, and at least one organic species R comprising two quaternary nitrogen atoms, the mixture preferably having the following molar composition:

| | |
|---|---|
| $XO_2/Y_2O_3$ | at least 2, preferably at least 20, more preferably 55 to 600; |
| $H_2O/XO_2$ | 1 to 100, preferably 10 to 70; |
| $R/XO_2$ | 0.02 to 2, preferably 0.05 to 0.5; |
| $M_nO/XO_2$ | 0.001 to 1, preferably 0.005 to 0.5; | where X is one or more tetravalent element(s) selected from the group formed by the following elements: silicon, germanium and titanium, preferably silicon, where Y is one or more trivalent element(s) selected from the group formed by the following elements: aluminium, iron, boron, indium and gallium, preferably aluminium, and where M is one or more alkali and/or alkaline-earth metal(s) selected from lithium, sodium, potassium, rubidium, caesium, calcium, magnesium, barium and a mixture of at least two of these metals, preferably sodium.

R is an organic species having two quaternary nitrogen atoms acting as an organic template. Preferably, R is the nitrogen-containing compound 1,6-bis(methylpiperidinium) hexane, which has the following developed formula:

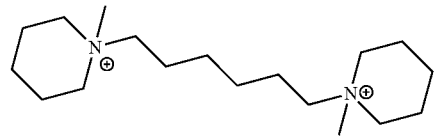 [SMILES: C[N+]1(CCCCCC[N+]2(C)CCCCC2)CCCCC1]

The anions associated with the quaternary ammonium cations present in the organic species template for synthesis of the IZM-2 zeolite present in the catalyst of the invention are selected from the acetate anion, the sulphate anion, the carboxylate anion, the tetrafluoroborate anion, halide anions such as the fluoride, the chloride, the bromide, the iodide, the hydroxide anion and a combination of several of these. Preferably, the anions associated with the quaternary ammonium cations present in the template species for synthesis of the IZM-2 zeolite are selected from the hydroxide anion and the bromide anion. Said organic nitrogen-containing species used as the template for the IZM-2 zeolite is synthesized using any method which is known to the skilled person. For the synthesis of 1,6-bis(methylpiperidinium)hexane dibromide, one mole of 1,6-dibromohexane is mixed with at least 2 moles of N-methylpiperidine in ethanol. Generally, the mixture is heated under reflux for a period in the range 3 to 10 hours. After filtration, then precipitation using an etherified solvent such as diethylether then re-crystallization from an ethanol/ether mixture, 1,6-bis(methylpiperidinium)hexane dibromide is obtained. 1,6-bis(methylpiperidinium)hexane dihydroxide is preferably obtained by treatment, at ambient temperature, of an aqueous solution of the 1,6-bis(methylpiperidinium)hexane dibromide using silver oxide, $Ag_2O$.

The source of the element X employed to carry out the process for preparing the IZM-2 zeolite may be any compound comprising the element X and which can liberate that element in aqueous solution in the reactive form. Advantageously, when the element X is silicon, the silica source may be any one of those currently used in synthesizing zeolites, for example solid powdered silica, silicic acid, colloidal silica, dissolved silica or tetraethoxysilane (TEOS). Examples of powdered silicas which may be used are precipitated silicas, in particular those obtained by precipitation from a solution of an alkali metal silicate, such as aerosil silicas, pyrogenic silicas, for example "CAB-O-SIL", and silica gels. It is possible to use colloidal silicas having different particle sizes, for example with a mean equivalent diameter in the range 10 to 15 nm or between 40 and 50 nm, such as those sold under trade names such as "LUDOX". Preferably, the silicon source is LUDOX-HS-40.

The source of element Y which may optionally be used to carry out the process for the preparation of the IZM-2 zeolite may be any compound comprising the element Y which can liberate that element in aqueous solution in the reactive form. In the preferred case in which Y is aluminium, the source of alumina is preferably sodium aluminate, or an aluminium salt, for example the chloride, nitrate, hydroxide or sulphate, an aluminium alkoxide or alumina proper, preferably in the hydrated or hydratable form, such as colloidal alumina, pseudoboehmite, gamma alumina or alpha or beta trihydrate. It is also possible to use mixtures of the sources cited above.

The source of the alkali and/or alkaline-earth metal M is advantageously a halide or a hydroxide of said metal M, preferably a hydroxide of said metal M.

In order to carry out the process for preparing the IZM-2 zeolite, it is preferable that the aqueous mixture comprising at least one source of at least one oxide $XO_2$, at least one source of at least one oxide $Y_2O_3$, at least one source of at least one alkali and/or alkaline-earth metal, and at least one organic species R containing two quaternary nitrogen atoms, also comprises at least one source of hydroxide ions. Said source of hydroxide ions advantageously derives from the organic template species R when it is in the hydroxide form, namely 1,6-bis(methylpiperidinium)hexane dihydroxide, or a source of alkali metal and/or alkaline-earth metal M when it is in the hydroxide form, for example sodium hydroxide.

Additionally, in accordance with a preferred implementation of the process for preparing the IZM-2 zeolite present in the catalyst of the invention, an aqueous mixture comprising an oxide of silicon, alumina, 1,6-bis(methylpiperidinium) hexane dibromide and sodium hydroxide is reacted.

The process for preparing the IZM-2 zeolite present in the catalyst of the invention consists of preparing an aqueous reaction mixture known as a gel and comprising at least one source of at least one oxide $XO_2$, at least one source of at least one oxide $Y_2O_3$, at least one organic species R, and at least one source of at least one alkali and/or alkaline-earth metal. The quantities of said reagents are adjusted so as to provide said gel with a composition allowing it to crystallize into IZM-2 zeolite in the as-synthesized form with general formula (I): $XO_2$: $aY_2O_3$: $bM_nO$; cR; $dH_2O$, where a, b and n satisfy the criteria defined above, c represents the number of moles of R and is in the range 0.005 to 2, preferably in the range 0.01 to 0.5, and d represents the number of moles of $H_2O$ and is in the range 0.005 to 2, preferably in the range 0.01 to 1. Next, the gel undergoes a hydrothermal treatment until the IZM-2 zeolite forms. The gel is advantageously subjected to hydrothermal conditions under autogenous reaction pressure, optionally by adding gas, for example nitrogen, at a temperature in the range 120° C. to 200° C., preferably in the range 140° C. to 180° C., and more preferably in the range 160° C. to 175° C. until solid IZM-2 zeolite crystals are formed in the as-synthesized form. The time necessary to obtain crystallization generally varies between 1 hour and several months depending on the composition of the reagents in the gel, the stirring and the reaction temperature. Preferably, the crystallization period is in the range 2 hours to 21 days. The reaction is generally carried out with stirring or in the absence of stirring, preferably in the presence of stirring.

It may be advantageous to add seeds to the reaction mixture to reduce the time necessary for the formation of crystals and/or to reduce the total crystallization period. It may also be advantageous to use seeds to encourage the formation of the IZM-2 zeolite to the detriment of impurities. Such seeds comprise solid crystals, especially crystals of IZM-2 zeolite. The crystalline seeds are generally added in a proportion in the range 0.01% to 10% by weight of oxide $XO_2$ used in the reaction mixture.

At the end of the hydrothermal treatment step resulting in crystallization of the IZM-2 zeolite, the solid phase is filtered and washed to obtain the IZM-2 zeolite in its as-synthesized form which is then dried and calcined to obtain the zeolite in the calcined form. The calcining step is advantageously implemented by means of one or more heating steps carried out at a temperature in the range 100° C. to 1000° C., preferably in the range 400° C. to 650° C., for a period in the range from a few hours to several days, preferably in the range 3 hours to 48 hours. Preferably, calcining is carried out in two consecutive heating steps. At the end of said calcining step, the IZM-2 zeolite obtained is that with an X ray diffraction diagram including at least the peaks set out in Table 1. It is free of water and of the organic species R present in the IZM-2 zeolite in the as-synthesized form.

In a first implementation of the process for the preparation of the catalyst of the invention, said catalyst is prepared using a process comprising at least the following steps:
 a) treatment of the IZM-2 zeolite in its calcined form by at least one ion exchange in order to obtain said zeolite in the hydrogen form;
 b) forming said zeolite in the hydrogen form with at least one porous mineral matrix;
 c) calcining the solid derived from said step b).

In step a) of said first implementation, the calcined IZM-2 zeolite prepared in accordance with the process described hereinabove undergoes one or more ion exchange(s) with a solution containing at least one ammonium salt, for example ammonium nitrate $NH_4NO_3$, in order to eliminate at least a portion, preferably practically all of the alkali/alkaline-earth cation(s) present in the calcined IZM-2 zeolite. A subsequent step for calcining in a stream of dry air at a temperature which is generally in the range 400° C. to 500° C. is intended to generate the formation of protons in the zeolite by desorption of ammonia, thus resulting in the hydrogen form of the zeolite. Said zeolite is thus an acid zeolite containing 70% to 100%, preferably in the range 80% to 100% and more preferably in the range 85% to 100% of compensating cations with the protonic form, $H^+$, the remainder of the cations being selected from metals from groups IA and IIA of the periodic classification of the elements; more particularly, said cation is selected from the cations $Na^+$, $Li^+$, $K^+$, $Rb^+$, $Cs^+$, $Ba^{2+}$, $Mg^{2+}$ and $Ca^{2+}$.

In step b) of said first implementation of the process for the preparation of the catalyst of the invention, the IZM-2 zeolite in the hydrogen form is shaped using any technique known to the skilled person. In particular, it may be mixed with at least one porous mineral matrix, generally amorphous, for example with a wet alumina gel powder. The mixture is then formed, for example by extrusion through a die. Forming may be carried out with matrixes other than alumina, such as magnesia, amorphous silica-aluminas, natural clays (kaolin, bentonite, sepiolite, attapulgite), silicas, titanium oxide, boron oxide, zirconia, phosphates of aluminium, phosphates of titanium, phosphates of zirconium, charcoal and mixtures thereof. Preferably, matrixes containing alumina in any of its forms known to the skilled person are used, more preferably gamma alumina. It is also advantageously possible to use mixtures of alumina and silica, mixtures of alumina and of silica-alumina. Techniques other than extrusion, such as pelletization or bowl granulation, may be used. The conditions for forming the IZM-2 zeolite, the choice of matrix, any prior milling of the zeolite, the peptization process, addition of pore-forming agents, the mixing time, the extrusion pressure if the catalyst is in the form of extrudates, and the drying speed and time are determined for each matrix as a function of rules which are well known to the skilled person, in order to obtain a catalyst that is preferably in the form of extrudates or beads.

In accordance with said step c) of said first implementation of the process for the preparation of the catalyst of the invention, the formed solid derived from said step b) undergoes a calcining step carried out at a temperature in the range 250° C. to 600° C., preferably in the range 400° C. to 550° C. Preferably, said calcining step is preceded by a drying step carried out at a temperature in the range 40° C. to 250° C., preferably in the range 80° C. to 200° C.

In a variation of said first implementation of the preparation process, the protons present in the IZM-2 zeolite in the hydrogen form derived from said step a) are exchanged at least in part, preferably completely, during a step a') using cations belonging to the alkali and alkaline-earth metal family. In particular, the protons present in said IZM-2 zeolite in the hydrogen form derived from said step a) are exchanged with $Li^+$, $Na^+$, $K^+$, $Rb^+$, $Cs^+$, $Mg^{2+}$, $Ca^{2+}$ or $Ba^{2+}$, preferably with $Na^+$ or $Cs^+$. Said step a'), which precedes said step b), may be carried out using any technique that is known to the skilled person, in particular by impregnation in excess or by ion exchange using methods which are well known to the skilled person, preferably by ion exchange(s). The IZM-2 zeolite obtained at the end of said step a') is thus basic: the cations it contains are mainly cations selected from the cations $Li^+$, $Na^+$, $K^+$, $Rb^+$, $Cs^+$, $Mg^{2+}$, $Ca^{2+}$ and $Ba^{2+}$, preferably from the cations $Na^+$ and $Cs^+$. Said IZM-2 zeolite in the basic form may contain different cations selected from $Li^+$, $Na^+$, $K^+$, $Rb^+$, $Cs^+$, $Mg^{2+}$, $Ca^{2+}$ and $Ba^{2+}$; in particular it may contain the cations $Cs^+$ and $Na^+$. It may also contain one or more cation(s) selected from the cations $Li^+$, $Na^+$, $K^+$, $Rb^+$, $Cs^+$, $Mg^{2+}$, $Ca^{2+}$ and protons which are present in a proportion of less than 30% of the total number of cations present in said IZM-2 zeolite in the basic form. Said step a') is carried out by bringing said IZM-2 zeolite in its acid form derived from said step a) into contact with a solution containing at least one precursor of the metal(s) belonging to the alkali and alkaline-earth metal family, preferably at least one precursor of metal(s) selected from Li, Na, K, Rb, Cs, Mg, Ca and Ba, and highly preferably at least one precursor of sodium or caesium. Examples of precursors used to carry out said step a') which may be cited are metal oxides and their mixtures in any proportions as well as salts of alkali and alkaline-earth metals, especially halide, sulphate, nitrate, phosphate, carbonate, oxalate, hydroxide, acetate, alcoholate, perchlorate, carboxylate or acetylacetonate salts. When the protons present in said IZM-2 zeolite in its acid form derived from said step a) are exchanged with $Cs^+$ cations, caesium acetate or caesium nitrate is advantageously used. These precursors may be in the form of a powder or be formed, or be soluble or insoluble in the reaction medium. In accordance with said variation of said first implementation, step a') is followed by calcining of the IZM-2 zeolite exchanged in the basic form at a temperature in the range 250° C. to 600° C. before proceeding to carry out said step b).

In accordance with said first implementation of said process for the preparation of the catalyst of the invention, the IZM-2 zeolite in its acid form derived from said step a), or the IZM-2 zeolite in the basic form from said step a') when the variation is employed, advantageously undergoes one or more treatment(s) which are known to the skilled person aimed at stabilizing, dealuminating or passivating said zeolite.

In accordance with a second implementation of the process for the preparation of the catalyst of the invention, said catalyst is prepared using a process comprising at least the following steps:

d) forming said IZM-2 zeolite with at least one porous mineral matrix;

e) calcining the solid derived from said step d);

f) treatment of the solid derived from said step e) in at least one ion exchange step in order to obtain said zeolite in a form such that the value taken by b in the formula: $XO_2$: $aY_2O_3$: $bM_nO$ is zero or in the range 0.005 to 0.5, a and n having the values given above in the present description, X, Y and M also having being defined above in the present description;

g) calcining the solid derived from said step f).

In accordance with step d) of said second implementation of the process for the preparation of the catalyst of the invention and in a first variation, for said forming step, a IZM-2 zeolite is used in the as-synthesized form, prepared in accordance with the process described above in the present description. Said zeolite in its as-synthesized form still comprises the organic template, which will be eliminated from the zeolite by calcining in accordance with said step e), and at least one type of alkali and/or alkaline-earth cations, preferably sodium. In a second variation, for said forming step, the IZM-2 zeolite used is in its calcined form, prepared in accordance with the process described above in the present description.

Forming said IZM-2 zeolite in its as-synthesized or calcined form may be carried out using any technique which is known to the skilled person. It may in particular be mixed with at least one porous mineral matrix, generally amorphous, for example with a moist alumina gel powder. The mixture is then formed, for example by extrusion through a die. Forming may be carried out with matrixes other than alumina, such as magnesia, amorphous silica-aluminas, natural clays (kaolin, bentonite, sepiolite, attapulgite), silicas, titanium oxide, boron oxide, zirconia, phosphates of aluminium, phosphates of titanium, phosphates of zirconium, charcoal and mixtures thereof. Preferably, matrixes containing alumina in any form known to the skilled person may be used, more preferably gamma alumina. Advantageously again, it is possible to use mixtures of alumina and silica, or mixtures of alumina and silica-alumina. Techniques other than extrusion, such as pelletization or bowl granulation, may be used. The conditions for forming the IZM-2 zeolite, the choice of the matrix, any prior milling of the zeolite, the peptization process, the addition of pore-forming agents, the mixing time, the extrusion pressure if the catalyst is formed into extrudates, and the speed and time of drying are determined for each matrix using rules that are well known to the skilled person in order to obtain a catalyst which is preferably in the form of extrudates or beads.

In accordance with step e) of said second implementation of the process for preparing a catalyst in accordance with the invention, the solid derived from said step d) undergoes a step for calcining carried out at a temperature in the range 250° C. to 600° C., preferably in the range 400° C. to 550° C. Said calcining step eliminates the organic template occluded in the pores of said as-synthesized IZM-2 zeolite when forming step d) is carried out on the IZM-2 zeolite in its as-synthesized form.

In accordance with step f) of said second implementation of the process for the preparation of the catalyst of the invention, and in a first variation, said calcined and formed zeolite derived from said step e) undergoes at least one ion exchange step in order to obtain said zeolite in a hydrogen form. Said zeolite in the hydrogen form contained in the catalyst of the invention then has the formula: $XO_2$: $aY_2O_3$ where X, Y and a are as defined above in the present description. Obtaining the IZM-2 zeolite in the hydrogen formed is accomplished using an identical protocol and similar operating conditions to those described for carrying out said step a) of said first implementation of the process for the preparation of the catalyst of the invention.

In accordance with a second variation of the implementation of said step f) of said second implementation of the process for the preparation of the catalyst of the invention, said calcined and formed zeolite derived from said step e) undergoes at least one ion exchange step in order to obtain said zeolite in a basic form with formula: $XO_2$: $aY_2O_3$: $bM_nO$ where X, Y, M, n and a are as defined above in the present description and b is in the range 0.005 to 0.5. Said zeolite derived from said step e) undergoes at least one ion exchange treatment with cations belonging to the family of alkali and alkaline-earth metals, preferably with cations selected from the cations $Li^+$, $Na^+$, $K^+$, $Rb^+$, $Cs^+$, $Mg^{2+}$, $Ca^{2+}$ or $Ba^{2+}$, and most preferably by $Cs^+$ cations. Advantageously and in accordance with said second variation, the $Na^+$ cations present in the IZM-2 zeolite derived from said step e) are exchanged by $Cs^+$ cations. This ion exchange is carried out using any technique which is known to the skilled person. Said second implementational variation of said step f) is carried out by bringing said IZM-2 zeolite, calcined and formed, derived from said step e) into contact with a solution containing at least one precursor of the metal(s) belonging to the alkali and alkaline-earth metal family, preferably at least one precursor of the metal(s) selected from Li, Na, K, Rb, Cs, Mg, Ca and Ba, and most preferably at least one precursor of caesium. Examples of precursors employed to carry out said second variation which may be cited are metallic oxides and their mixtures in any proportions as well as salts of alkali and alkaline-earth metals, especially halide, sulphate, nitrate, phosphate, carbonate, oxalate, hydroxide, acetate, alcoholate, perchlorate, carboxylate or acetylacetonate salts. When the zeolite derived from said step e) is exchanged with $Cs^+$ cations, caesium acetate or caesium nitrate is advantageously employed. These precursors may be in the powder form or formed, and soluble or insoluble in the reaction medium. Said treatment carried out in accordance with said second implementational variation of said step f) may comprise one or more successive ion exchanges.

In accordance with said step g) of said second implementation of the process for the preparation of the catalyst of the invention, the exchanged and formed zeolite from said step f) undergoes a treatment by calcining carried out at a temperature in the range 250° C. to 600° C.

In accordance with said second implementation of the process for the preparation of the catalyst of the invention, said step g) is advantageously followed by a step h) consisting of carrying out a treatment comprising at least one ion exchange of protons present in the IZM-2 zeolite in its hydrogen form so as to obtain a catalyst comprising a IZM-2 zeolite in the basic form. Said step h) is advantageously carried out when a catalyst comprising a IZM-2 zeolite in the basic form is desired for a particular application and step f) results in obtaining a zeolite in the hydrogen form. Said step h) is carried out using a protocol and operating conditions which are identical to those described for carrying out said step a') of said first implementation of the process for the preparation of the catalyst of the invention. Said step h) is then followed by a step for calcining at a temperature in the range 250° C. to 600° C.

In accordance with said second implementation of said process for the preparation of a catalyst of the invention, one or more treatment(s) which is (are) known to the skilled person is (are) advantageously carried out with the intention of stabilizing, dealuminating or passivating the zeolite.

When the catalyst of the invention comprises at least one additional metal selected from metals from groups IIIb, IVa and IVb, deposition of at least said metal may be carried out at any time during the preparation of one or the other implementations of the preparation process described above in the present description, either before forming or during mixing of the zeolite and the matrix, the zeolite being mixed with the ensemble constituted by the precursor(s) of said metal(s) and the matrix or, as is preferable, after forming. Said added metal(s) is (are) generally deposited either practically completely on the zeolite or in part on the zeolite and in part on the matrix or, as is preferable, practically completely on the matrix, this being carried out, in a manner which is known to the skilled person, by judicious choice of the parameters employed during said deposition, such as the nature of the precursor of said metal(s), for example. The deposit of at least one metal selected from metals from groups IIIb, IVa and IVb may be accomplished using any deposition technique known to the skilled person, in particular by dry impregnation, excess impregnation or ion exchange techniques, preferably by ion exchange(s). Any metallic precursor would be suitable for introducing said metal.

The catalyst of the invention is advantageously used to carry out various processes for the transformation of hydrocarbon feeds.

In particular, in another aspect, the invention provides a process for the production of at least one alcoholic ester from at least one compound belonging to the triglycerides family and at least one compound carrying an alcohol function carried out in the presence of at least one catalyst of the invention as described hereinabove in the present description. The reaction employed in said process for the production of at least one alcoholic ester is a reaction for transesterification of esters. Said compound carrying an alcohol function preferably contains a single alcohol function. Carrying out said process results in the production of a first organic phase essentially constituted by at least said alcoholic ester and a second organic phase essentially constituted by glycerol, said second phase being termed the glycerin phase because of the impurities present therein. The alcoholic ester present in said first organic phase is used as a fuel and more precisely as a biodiesel. It satisfies the specifications of standard EN14214 (vegetable oil ester content more than 96.5%). Current specifications impose an alcoholic ester yield of at least 96.5% by weight, the yield of alcoholic ester being calculated as being equal to the percentage by weight of said ester in said first organic phase which may contain a very small amount of the initial compound belonging to the triglycerides family and/or intermediate compounds, in particular compounds (esters) belonging to the monoglycerides and diglycerides family. Preferably, the initial compound belonging to the triglycerides family does not represent more than 0.2% by weight of said first organic phase, the compounds belonging to the monoglycerides family does not represent more than 0.8% by weight of said first organic phase, the compounds belonging to the diglycerides family do not represent more than 0.2% by weight of said first organic phase and the glycerine does not represent more than 0.25% by weight of said first organic phase. Said second organic phase contains 95% to 99.9% by weight of glycerol and preferably 98% to 99.9% by weight of glycerol. Said second organic phase thus has a maximum glycerol purity. The process for the production of at least one alcoholic ester of the invention results in the production of a fuel ester which satisfies the specifications and a high purity glycerin by operating in one or two steps in accordance with a process which functions continuously or batchwise, as will be described below in the present description. Further, the alcoholic ester and the glycerol produced contain no impurities derived from the catalyst used to implement the transesterification process of the invention. In addition, no purification treatment of one or the other organic phase is necessary.

Using a catalyst in accordance with the invention in the process for the production of at least one alcoholic ester is particularly advantageous in that it has a good lixiviation behaviour, which is verified by the absence of trace metals deriving from the catalyst (silicon, aluminium, metal(s) present in the IZM-2 zeolite following an ion exchange step) both in the alcoholic ester formed and present in said first organic phase and in the glycerin produced and constituting said second organic phase. The recyclability or service life of the catalyst of the invention, evaluated experimentally over time, is satisfactory (several hundred hours) when it is used in the process for the production of at least one alcoholic ester in accordance with the invention.

The process for the production of at least one alcoholic ester in accordance with the invention starting from at least one compound belonging to the triglycerides family and at least one compound carrying an alcohol function is carried out in accordance with a variety of implementations. Irrespective of the implementation selected, said process is advantageously carried out at a temperature in the range 130° C. to 220° C., at a pressure of less than 10 MPa, more precisely under autogenous pressure, and with a molar excess of the compound carrying the alcohol function with respect to the stoichiometry (compound belonging to the triglycerides family/compound carrying an alcohol function). Depending on the process employed for the production of at least one alcoholic ester in accordance with the invention, the molar ratio (compound carrying an alcohol function/compound belonging to the triglycerides family) is more than 3. Preferably, the process for the production of at least one alcoholic ester in accordance with the invention is carried out by bringing 15 to 35 and more preferably 25 to 35 moles of said compound carrying an alcohol function into contact with 1 mole of said compound belonging to the triglycerides family, i.e. a molar excess in the range 15 to 35, preferably in the range 25 to 35. By operating at a temperature of 220° C. or less, an alcoholic ester is generally obtained with the same colour as the reactive compound belonging to the triglycerides family and a glycerin which is colourless after decanting, as will be described below.

A first mode of carrying out the process for the production of at least one alcoholic ester in accordance with the invention consists of carrying out said process in a batch process using at least one closed, or batch, reactor. In accordance with said first implementation, the process may be carried out in one or two steps. For a two-step implementation, the first step is carried out under conditions such that the yield of alcoholic ester at the end of said first step is in the range 85% to 95% by weight, then the effluent derived from said first step is cooled by evaporating off the excess compound carrying said alcohol function, the phase formed of glycerin is allowed to decant then the second step is carried out by re-heating the reaction mixture formed by the organic phase containing the alcoholic ester, the initial compound belonging to the triglycerides family and the intermediate compounds belonging to the monoglycerides and diglycerides families, the compound carrying said alcohol function being re-introduced into said reaction mixture. Said second step can increase the yield of alcoholic ester beyond 96.5% by weight. Preferably, the yield of alcoholic ester is at least 98% by weight. The first and the second steps which each carry out a transesterification reaction are carried out at a temperature in the range 130° C. to 220° C., the second step being carried out at a temperature which is advantageously equal to or higher than that of the first step and at a pressure corresponding to the autogenous pressure of the medium.

For the one-step implementation, the operating conditions are adapted so that the yield of alcoholic ester at the end of said step is at least 96.5%, preferably at least 98%. In order to obtain that high a yield in a single step, the operation is generally carried out at a temperature and a molar ratio (compound carrying an alcohol function/compound belonging to the triglycerides family) which are higher than the temperatures and molar ratios applied for the two-step process. Advantageously, for a one-step process, the temperature is in the range 175° C. to 220° C. and the molar ratio (compound carrying an alcohol function/compound belonging to the triglycerides family) is more than 30.

A second implementation of the process for the production of at least one alcoholic ester in accordance with the invention consists of carrying out said process continuously, i.e. the production of said alcoholic ester is continuous. This implementation requires the use of several autoclave reactors where the transesterification reaction is carried out, and several decanters for decanting the two organic phases, one comprising the alcoholic ester and the other formed by the glycerin. It is advantageous to operate the process continuously in two steps: in a first step, a transesterification reaction is carried out in an autoclave reactor under conditions such that the yield of alcoholic ester is close to 85%, preferably 90% by weight, then it is decanted by evaporating off the compound carrying said alcohol function and cooling; in a second autoclave reactor, a second transesterification reaction is carried out by adding, to the organic phase of the reaction medium comprising the alcoholic ester derived from said first step, a portion of the compound carrying the previously evaporated alcohol function in order to hone the performances of the process for the production of at least one alcoholic ester by increasing the yield of said ester in said second step. Finally, the excess compound carrying said alcohol function is evaporated off and the glycerin and esters are separated out (mono- and di-glycerides are also esters) by decanting. Preferably, for each of the two steps, at least one fixed bed reactor is used, operating at a temperature in the range 130° C. to 220° C., preferably in the range 150° C. to 180° C., at a pressure in the range 1 to 7 MPa, a HSV (volume of phase comprising at least the compound from the triglycerides family/volume of catalyst/h) in the range 0.1 to 3 $h^{-1}$, preferably in the range 0.3 to 2 $1^{-1}$, and a weight ratio (compound carrying an alcohol function/compound belonging to the triglycerides family) between 3/1 and 0.1/1.

A particular and advantageous implementation of the continuous process consists of introducing the compound carrying the alcohol function in a fractional manner into each of the reactors. In general, tube reactors are selected for this implementation. in particular, it is advantageous to introduce said compound carrying the alcohol function into two locations of a tube reactor: as an example, all of the compound belonging to the triglycerides family and ⅔ of the volume of the total quantity of the compound carrying the alcohol function are introduced into the reactor inlet then the remaining quantity of the compound carrying the alcohol function is introduced to the final third of the depth of the catalytic bed.

In accordance with said process for the production of at least one alcoholic ester in accordance with the invention, the catalyst used comprises at least one IZM-2 zeolite either in the hydrogen form or in the basic form. When said zeolite is in the basic form, said zeolite has been exchanged with cations belonging to the family of alkali and alkaline-earth metals, preferably with cations selected from the cations $Li^+$, $Na^+$, $K^+$, $Rb^+$, $Cs^+$, $Me^+$, $Ca^{2+}$ or $Ba^{2+}$, more preferably by $Cs^+$ cations.

Fats

In accordance with the process for the production of at least one alcoholic ester in accordance with the invention, the compound belonging to the triglycerides family is a fat. The fats used in the process of the invention correspond to natural or synthetic substances, of animal or vegetable origin, mainly containing triglycerides, customarily termed oils and fats. Examples of oils that may be used which may be cited are all regular oils such as palm oils (solids or oleins), soya, palm kernel, coprah, babassu, rape (old or new), sunflower (conventional or oleic), corn, cottonseed, peanut oils, Barbados nut (Jatropha curcas), castor oil, linseed and crambe oils and any oils derived, for example, from sunflower or from rapeseed, by genetic modification or hybridization or from algae or micro-algae. It is also possible to use frying oils, slaughterhouse oils, various animal oils, such as fish oil, seal oil, slaughterhouse oil, tallow, suet, or fats from the treatment of waste water and even poultry fats, since the esters manufactured from certain alcohols such as ethyl alcohol, isopropyl alcohol or butyl alcohol, means that more than 10° C. can be gained in the pour point and as a result more saturated oils can be used. Examples of oils which can also be indicated are oils which have been partially modified, for example by polymerization or oligomerization, such as "stand oils" from linseed oil, sunflower seed oil and blown vegetable oils, stand oils being known to the skilled person to be partially polymerized oils. The oils used are neutral or acidic, virgin or recycled.

In the transesterification process of the invention, the presence of fatty acid in the oils is not, a priori, prejudicial as catalytic systems based on IZM-2 zeolite, exchanged or otherwise, are also active in esterification and also transform fatty acids into esters. The limiting value of free fatty acids contained in the oils have an acid index of close to 10 (the acid index being defined as the mass in mg of KOH necessary to assay all of the free fatty acids in 1 g of oil). The operability of the process under these conditions is close to that defined with an oil with a low acid index (i.e. less than 0.2 mg of KOH/g) in general use. In the case of oils with a very high acid index (close to 10 mg of KOH/g), one of the possibilities is to precede the transesterification reaction by a reaction for esterification of the free fatty acids present, either using the same alcohol as that used in the transesterification process in the presence of the catalyst of the invention in which the IZM-2 zeolite is preferably in the protonated form, or, as is preferable, using glycerin, to form a total or partial glycerol ester, using the same catalyst based on IZM-2 as that used for the transesterification reaction, at atmospheric pressure and preferably under vacuum and at temperatures in the range 150° C. to 220° C.

When using frying oils, which constitute a very cheap raw material for producing biodiesel, it is necessary to eliminate fatty acid polymers from the reaction mixture so that the mixture of esters satisfies the specifications of standard EN 14214.

Alcohol

In accordance with a process for the production of at least one alcoholic ester of the invention, the nature of the compound carrying an alcohol function plays a role in the activity of the transesterification reaction and as a consequence on the conversion of triglycerides. Highly preferably, said compound carrying an alcohol function is a monoalcohol and still more preferably an aliphatic monoalcohol containing 1 to 18 carbon atoms, preferably 1 to 12 carbon atoms and more preferably 1 to 5 carbon atoms.

Preferably, the compound carrying the alcohol function is methyl alcohol (methanol) which is the alcohol which results in the best conversion of triglycerides. Furthermore, ethyl alcohol and isopropyl, propyl, butyl, isobutyl and even amyl alcohol are advantageously used. Heavier alcohols such as ethylhexyl alcohol or lauryl alcohol may also be envisaged for carrying out the transesterification process of the invention. Advantageously, methyl alcohol may be added to the heavy alcohols to facilitate the reaction. Further, when the ethyl ester is prepared, a mixture of ethyl alcohol and methyl alcohol may be used, comprising 1% to 50% by weight, preferably 1% to 10% by weight of methyl alcohol, in order to augment conversion.

In a further aspect, the invention pertains to a process for the transformation of at least one aliphatic compound containing 1 to 18 carbon atoms and carrying an alcohol function, said process being carried out in the presence of at least one catalyst of the invention, which comprises at least one IZM-2 zeolite preferably in its hydrogen form.

Preferably, said aliphatic compound carrying an alcohol function comprises 1 to 12 carbon atoms, more preferably 1 to 6 carbon atoms. More preferably, said aliphatic compound carrying an alcohol function is selected from methanol and ethanol. Said aliphatic compound containing 1 to 18 carbon atoms and carrying an alcohol function may be linear or branched. Preferably, it is a monoalcohol. It is not necessary to use completely anhydrous alcohols for carrying out said process for transformation of at least one aliphatic compound containing 1 to 18 carbon atoms and carrying an alcohol function.

In accordance with a first implementation of said process for the transformation of at least one aliphatic compound containing 1 to 18 carbon atoms and carrying an alcohol function, said transformation which is carried out is a dehydration reaction during which said aliphatic compound carrying an alcohol function is dehydrated to olefin(s) with the production of water. In accordance with said first implementation, ethanol is preferably used as the aliphatic compound having an alcohol function in order to produce ethylene. The operating conditions for carrying out said process for the transformation of alcohols to olefins are as follows: the total pressure is less than 2 MPa, preferably in the range 0.05 to 1 MPa, the temperature is in the range 150° C. to 500° C., preferably in the range 200° C. to 350° C. The HSV, defined as being the flow rate at which the feed comprising said aliphatic compound is introduced divided by the mass of catalyst, varies in general between 0.5 and 50 $h^{-1}$, preferably between 1 and 25 $h^{-1}$. An inert gas such as nitrogen, for example, or a light hydrocarbon, may be used to dilute the feed comprising said aliphatic compound at the catalyst.

Said process for the transformation of alcohols to olefins in accordance with said first implementation is advantageously carried out in a fixed, moving or fluidized bed. Apart from the water generated during the dehydration reaction, the ethers associated with the alcohols introduced into the reactor may principally be formed in the case of methanol and ethanol. Said ethers may advantageously be recycled in order to increase the olefin yield.

In accordance with a second implementation of said process for the transformation of at least one aliphatic compound containing 1 to 18 carbon atoms and carrying an alcohol function, said transformation which is employed simultaneously carries out, in the same reactor, dehydration of said aliphatic compound to olefin(s) and oligomerization of said olefin(s). It produces hydrocarbons which will be incorporated into the gasoline pool and/or into the diesel pool. The operating conditions for carrying out such a transformation are such that the temperature is in the range 250° C. to 450° C., the total pressure is in the range 2 to 10 MPa and the HSV, corresponding to the mass flow rate at which the feed comprising said aliphatic compound is introduced divided by the mass of the catalyst, is in the range 0.1 to 5 $h^{-1}$. The increase in the pressure for carrying out said second implementation with respect to said first implementation (dehydration) encourages the formation of compounds derived from oligomerization of the olefins formed in situ in the reactor(s). The catalyst based on IZM-2 of the invention is preferably activated, preferably by calcining it, prior to bringing it into contact in the reactor with the feed comprising said aliphatic compound under the reaction conditions cited above. An inert gas such as nitrogen or a light hydrocarbon is advantageously used to dilute the feed at the catalyst.

A variation of said second implementation of the transformation process of the invention consists of separating the implementation of the dehydration step from that for the oligomerizationo of the olefins formed in the dehydration step. In accordance with said variation, a separator is advantageously installed between the reactor used for dehydration of the alcohols to olefins and the reactor used for transformation of the olefins into heavier compounds. The dehydration reaction and the oligomerization reaction may be carried out in the presence of a catalyst based on a IZM-2 zeolite of the invention or the dehydration reaction may be carried out in the presence of a catalyst comprising a zeolite that is different from the IZM-2 zeolite, a silica-alumina or an activated alumina, and the oligomerization reaction is carried out in the presence of a catalyst based on a IZM-2 zeolite of the invention.

Irrespective of the implementation employed for the transformation of a feed comprising at least one aliphatic compound carrying an alcohol function, the reaction for transformation of said feed by dehydration or by dehydration then oligomerization may be carried out in any type of reactor known to the skilled person. In accordance with a first implementation, said process for the transformation of said feed is carried out in at least one fixed bed reactor. The catalyst is then preferably located in a radial bed reactor in order to minimize the pressure drop across the catalytic bed. In a second implementation, said process for the transformation of said feed is carried out in at least one moving bed reactor. One or more reactors may be used with one or more moving beds, possibly with staggered injection of the feed, coupled or otherwise with a continuous regeneration system.

In accordance with said process for the transformation of a feed comprising at least one aliphatic compound carrying an alcohol function in accordance with the invention, the reaction effluent is held at its reaction pressure, not counting the pressure drops across the equipment through which it passes. The effluent is cooled to below the water dew point. Regarding said second implementation (dehydration+oligomerization), said cooled reaction effluent is introduced into a device that allows three-phase separation of a gas phase primarily constituted by light olefins, an organic liquid (gasoline and gas oil) and an aqueous liquid (water, non-transformed alcohol, dissolved hydrocarbons).

The present invention also pertains to a process for the oligomerization of an olefinic feed, consisting of bringing said feed into contact with at least one catalyst in accordance with the invention, which latter comprises at least one IZM-2 zeolite, preferably in its hydrogen form (protonated form, $H^+$). Said process can produce fuel, for example gasoline and/or kerosene and/or diesel and/or, more generally, a cut with a boiling point commencing at a temperature of more than 150° C.

Said olefinic feed contains hydrocarbon molecules containing 2 to 12 carbon atoms per molecule, preferably containing 2 to 7 carbon atoms per molecule. It contains 20% to 100% by weight, preferably 25% to 80% by weight of olefins.

The olefins present in the olefinic feed may derive from any source containing olefins containing 2 to 12 carbon atoms per mole, preferably 2 to 7 carbon atoms per mole. Said olefins may, for example, originate from a fluid catalytic cracking unit (FCC) and/or from a steam cracking unit, and/or from a unit for dehydrogenation of paraffins and/or a unit for the polymerizing dehydration of methanol to water and light olefins.

The oligomerization reaction may be carried out in the liquid phase, in the supercritical phase or in the gas phase in the presence of the catalyst of the invention in which the IZM-2 zeolite present therein is preferably in its hydrogen form.

Said oligomerization process of the invention is preferably carried out under the following operating conditions: the total pressure is in the range 0.1 to 10 MPa, preferably in the range 0.3 to 7 MPa, the temperature is in the range 40° C. to 600° C., preferably in the range 40° C. to 400° C.; the hourly space velocity, expressed as the volume of feed introduced per volume of catalyst per hour, is in the range 0.01 to 100 $h^{-1}$, preferably in the range 0.1 to 20 $h^{-1}$.

The present invention also pertains to a process for the production of phenylalkanes comprising a reaction for the alkylation of at least one aromatic compound by at least one linear olefin, said process being carried out in the presence of at least one catalyst in accordance with the invention comprising at least one IZM-2 zeolite, preferably in its acid form (protonated form, $H^+$). Advantageously, said catalyst is disposed in a fixed bed in at least one reaction zone carrying out said alkylation reaction.

In accordance with a first implementation of said process for the production of phenylalkanes, the aromatic compound is preferably benzene and the linear olefin used contains 2 or 3 carbon atoms in order to result in the production of ethylbenzene or cumene. Said process for the production of ethylbenzene or cumene is carried out by bringing benzene into contact with a feed comprising either ethylene or propylene. The alkylation reaction is normally carried out in the liquid phase, in the supercritical phase or in the gas phase. The operating conditions applied to carry out said process for the production of ethylbenzene or cumene are as follows: the temperature employed is in the range 30° C. to 300° C., preferably in the range 150° C. to 300° C., at an absolute pressure in the range 0.1 to 10 MPa, preferably in the range 2 to 7 MPa, with a flow rate of liquid hydrocarbons of 0.5 to 200 volumes per volume of catalyst per hour, and with a benzene/olefins molar ratio in the range 1:1 to 50:1, preferably in the range 3:1 to 7:1 for propylene and in the range 7:1 to 12:1 for ethylene.

In accordance with a second implementation of said process for the production of phenylalkanes, the aromatic compound is preferably benzene and the linear olefin used comprises 9 to 16 carbon atoms per mole, preferably 10 to 14 carbon atoms, to produce linear phenylalkanes or linear alkylbenzenes (LAB). Said process for the production of phenylalkanes is carried out by bringing benzene into contact with a feed comprising at least one linear olefin in at least one reaction zone containing said catalyst of the invention preferably functioning in a fixed bed mode. The operating conditions applied to carry out said process for the production of phenylalkanes of the invention are selected by the skilled person. The reaction zone is operated at a temperature which is advantageously below 400° C., preferably less than 350° C. and more preferably less than 300° C. and at a pressure of 1 to 10 MPa, preferably 2 to 6 MPa, with a liquid hydrocarbon flow rate (space velocity) of 0.5 to 80, preferably 0.5 to 50 volumes per volume of catalyst per hour. The benzene/olefins molar ratio is advantageously in the range 1 to 50, preferably in the range 10 to 30.

The present invention also pertains to a process for the disproportionation of toluene to produce benzene and xylenes carried out in the presence of at least one catalyst of the invention comprising at least one IZM-2 zeolite, preferably in the acid form (protonated form, $H^+$). Said catalyst has proved to be highly effective for said use, as it has proved to be particularly active, selective and stable.

The operating conditions applied to carry out said disproportionation process of the invention are generally as follows: a temperature in the range 250° C. to 650° C., preferably in the range 350° C. to 550° C.; a pressure in the range 1 to 6 MPa, preferably in the range 2 to 4.5 MPa; an hourly space velocity, expressed in kilograms of feed introduced per kilogram of catalyst per hour, in the range 0.1 to 10 $h^{-1}$, preferably in the range 0.5 to 4 $h^{-1}$; a molar ratio of hydrogen to hydrocarbons in the range 2 to 20, preferably in the range 3 to 12 mol/mol.

The following examples illustrate the present invention without limiting its scope.

EXAMPLES

Example 1

Preparation of 1,6-bis(methylpiperidinium)hexane dibromide for the Preparation of IZM-2 Zeolites (Z1 and Z2)

50 g of 1,6-dibromohexane (0.20 mole, 99%, Alfa Aesar) was added to a 1 L flask containing 50 g of N-methylpiperidine (0.51 mole, 99%, Alfa Aesar) and 200 mL of ethanol. The reaction medium was stirred and heated under reflux for 5 h. The mixture was then cooled to ambient temperature and filtered. The mixture was poured into 300 mL of cold diethylether, then the precipitate formed was filtered and washed with 100 mL of diethylether. The solid obtained was recrystallized from an ethanol/ether mixture. The solid obtained was vacuum dried for 12 h. 71 g of a white solid was obtained (i.e. a yield of 80%). The product had the expected $^1H$ NMR spectrum. $^1H$ NMR ($D_2O$, ppm/TMS): 1.27 (4H, m); 1.48 (4H, m); 1.61 (4H, m); 1.70 (8H, m); 2.85 (6H, s); 3.16 (12H, m).

Example 2

Preparation of an IZM-2 Zeolite (Z1)

30 g of a colloidal suspension of silica, known under the trade name HS-40 sold by Aldrich, was incorporated into a solution composed of 0.158 g of sodium aluminate (Carlo Erba), 2.433 g of sodium hydroxide (Prolabo), 14.7333 g of 1,6-bis(methylpiperidinium)hexane dibromide prepared in accordance with Example 1 and 101.561 g of deionized water. The molar composition of the mixture was as follows: $SiO_2$; 0.005 $Al_2O_3$; 0.17 $Na_2O$; 0.17 1,6-bis(methylpiperidinium) hexane; 33.33 $H_2O$. The mixture was stirred vigorously for half an hour. Following homogenization, the mixture was transferred into an autoclave. The autoclave was heated for 6 days at 170° C. with stirring (200 rpm). The crystalline product obtained was filtered, washed with deionized water (to a neutral pH) then dried overnight at 100° C. The solid was introduced into a muffle furnace where calcining was carried out: the calcining cycle comprised a temperature ramp-up to 200° C., a stage at 200° C. for 2 hours, a temperature ramp-up to 550° C. followed by a stage at 550° C. for 8 hours, then a return to ambient temperature.

The solid calcined product was analyzed by X ray diffraction and identified as being constituted by IZM-2 zeolite. This solid corresponded to a IZM-2 zeolite exchanged with $Na^+$ and was denoted Z1.

Example 3

Preparation of a Catalyst C1 Comprising a IZM-2 Zeolite in the Hydrogen Form and an Alumina Matrix (in Accordance with the Invention)

Catalyst C1 comprising a IZM-2 zeolite and alumina was manufactured as follows: 7 g of zeolite Z1 was mixed with 43 g of a matrix composed of an alumina gel sold under the trade mark SB3 by the supplier Condea Chemie GmbH. This powder mixture was then mixed with an aqueous solution containing 66% by weight nitric acid (7% by weight of acid per gram of dry gel) then mixed for 15 minutes. The mixed paste was extruded through a 1.2 mm diameter die. The extrudates were calcined at 500° C. (temperature ramp-up 5° C./min) for 2 hours in a traversed bed in dry air (1 L air/h/g of solid).

The calcined extrudates were exchanged three times in contact with an ammonium nitrate solution in order to obtain the IZM-2 zeolite in its acid form: 50 g of extrudates were brought into contact with 400 mL of a 10N solution of ammonium nitrate and the mixture was heated under reflux with stirring for 4 hours. The mixture was then filtered and the extrudates were rinsed with 800 mL of distilled water and oven dried in a thin layer overnight at 150° C. This operation was carried out three times. After the third exchange, the extrudates were calcined at 450° C. (temperature ramp-up 5° C./min) for two hours in a traversed bed with dry air (2 L air/h/gram of solid). This produced catalyst C1 which had a sodium content in the IZM-2 zeolite, measured by atomic adsorption on the exchanged and calcined extrudates, of less than 50 ppm by weight. The catalyst C1 comprised a IZM-2 zeolite in its acid form ($H^+$) with the molar composition $SiO_2$: 0.0057 $Al_2O_3$, i.e. a Si/Al ratio of 88. Said catalyst C1 was constituted by 19% by weight of IZM-2 zeolite in its acid form and 81% by weight of alumina.

Example 4

Preparation of a Catalyst C2 Comprising a IZM-2 Zeolite Exchanged with Caesium and an Alumina Matrix (in Accordance with the Invention)

The catalyst C2 comprising a IZM-2 zeolite and alumina was manufactured as follows: 7 g of zeolite Z1 was mixed with 43 g of a matrix composed of an alumina gel sold under the trade mark SB3 by the supplier Condea Chemie GmbH. This powder mixture was then mixed with an aqueous solution containing 66% by weight nitric acid (7% by weight of acid per gram of dry gel) then mixed for 15 minutes. The mixed paste was extruded through a 1.2 mm diameter die. The extrudates were calcined at 500° C. (temperature ramp-up 5° C./min) for 2 hours in a traversed bed in dry air (1 L air/h/g of solid).

The basic form of the IZM-2 zeolite exchanged with caesium present in the extrudates was prepared as follows: 50 g of the extrudates was brought into contact with 400 mL of a 0.3M solution of caesium nitrate and the mixture was heated under reflux for 4 hours, with stirring. This operation was repeated until the reaction medium had the pH of the initial caesium nitrate solution. The mixture was then filtered and the extrudates were rinsed with 800 mL of distilled water and dried in a thin layer overnight at 150° C. This operation was carried out three times. After the third exchange, the extrudates were calcined at 450° C. (temperature ramp-up 5° C./min) for two hours in a traversed bed with dry air (2 L air/h/g of solid). This produced catalyst C2 which had a sodium content in the IZM-2 zeolite, measured by atomic adsorption on the exchanged and calcined extrudates, of less than 50 ppm by weight. The catalyst C2 comprised a IZM-2 zeolite in the basic form exchanged with caesium with the composition $SiO_2$: 0.0057 $Al_2O_3$: 0.17 $Cs_2O$, i.e. a Si/Al ratio of 88. Said catalyst C2 was constituted by 19% by weight of IZM-2 zeolite in the basic form (Cs) and 81% by weight of alumina.

Example 5

Preparation of an IZM-2 Zeolite (Z2)

20.115 g of a colloidal suspension of silica, known under the trade name Ludox HS-40 sold by Aldrich, was incorporated into a solution composed of 0.422 g of sodium aluminate (Carlo Erba), 1.48 g of sodium hydroxide (Prolabo), 9.879 g of 1,6-bis(methylpiperidinium)hexane dibromide prepared in accordance with Example 1 and 68.104 g of deionized water. The molar composition of the mixture was as follows: $SiO_2$; 0.017 $Al_2O_3$; 0.17 $Na_2O$; 0.17 1,6-bis(methylpiperidinium)hexane; 33.33 $H_2O$. The mixture was stirred vigorously for half an hour. Following homogenization, the mixture was transferred into an autoclave. The autoclave was heated for 8 days at 170° C. with stirring (200 rpm). The crystalline product obtained was filtered, washed with deionized water (to a neutral pH) then dried overnight at 100° C. The solid was introduced into a muffle furnace where calcining was carried out: the calcining cycle comprised a temperature ramp-up to 200° C., a stage at 200° C. for 2 hours, a temperature ramp-up to 550° C. followed by a stage at 550° C. for 8 hours, then a return to ambient temperature.

The calcined solid was analyzed by X ray diffraction and identified as being constituted by IZM-2 zeolite. This solid corresponded to a IZM-2 zeolite exchanged with $Na^+$ and was denoted Z2.

Example 6

Preparation of a Catalyst C3 Comprising a IZM-2 Zeolite and an Alumina Matrix (in Accordance with the Invention)

The catalyst C3 comprising a IZM-2 zeolite and alumina was manufactured as follows: 7 g of IZM-2 zeolite (Z2) was mixed with 43 g of a matrix composed of an alumina gel sold under the trade mark SB3 by the supplier Condea Chemie GmbH. This powder mixture was then mixed with an aqueous solution containing 66% by weight nitric acid (7% by weight of acid per gram of dry gel) then mixed for 15 minutes. The mixed paste was extruded through a 1.2 mm diameter die. The extrudates were calcined at 500° C. (temperature ramp-up 5° C./min) for 2 hours in a traversed bed in dry air (1 L air/h/g of solid).

The calcined extrudates were exchanged three times in contact with an ammonium nitrate solution in order to obtain the IZM-2 zeolite in its acid form: 50 g of extrudates were brought into contact with 400 mL of a 10N solution of ammonium nitrate and the mixture was heated under reflux with stirring for 4 hours. The mixture was then filtered and the extrudates were rinsed with 800 mL of distilled water and oven dried in a thin layer overnight at 150° C. This operation was carried out three times. After the third exchange, the extrudates were calcined at 450° C. (temperature ramp-up 5° C./min) for two hours in a traversed bed with dry air (2 L air/h/gram of solid).

This produced catalyst C3 which had a sodium content in the IZM-2 zeolite, measured by atomic adsorption on the exchanged and calcined extrudates, of less than 50 ppm by weight. The catalyst C3 comprised a IZM-2 zeolite in its acid form ($H^+$) with the molar composition $SiO_2$: 0.0263 $Al_2O_3$, i.e. a Si/Al ratio of 19. Said catalyst C3 was constituted by 19% by weight of IZM-2 zeolite in its acid form and 81% by weight of alumina.

Example 7

Transesterification of Vegetable Oils (Rapeseed Oil) by Methanol in the Presence of Catalyst C1 (in Accordance with the Invention)

This example employed a batch transesterification process in a closed reactor. The oil used was rapeseed oil which had an acid index measured as 0.1 mg KOH/g of oil and a fatty acid composition as shown in Table 2. The figure following the colon (:) in the symbol Cx:y in the column "nature of fatty chain" corresponded to the number of unsaturated bonds (double bonds) in the molecules present in each of the fatty acid glycerides and the figure following the letter C corresponds to the number of carbon atoms of the molecules present in each of the fatty acid glycerides.

TABLE 2

| Composition of rapeseed oil | | |
|---|---|---|
| Fatty acid glyceride | Nature of fatty chain | % by weight |
| Palmitic | C16:0 | 5 |
| Palmitoleic | C16:1 | <0.5 |
| Stearic | C18:0 | 2 |
| Oleic | C18:1 | 59 |
| Linoleic | C18:2 | 21.5 |
| Linolenic | C18:3 | 9 |
| Arachidic | C20:0 | <0.5 |
| Gadoleic | C20:1 | 1 |
| Behenic | C22:0 | <0.5 |
| Erucic | C22:1 | <1 |

25 g of rapeseed oil, 17 g of methanol and 1 g of catalyst C1 were introduced into a closed reactor at ambient temperature. The methanol/oil weight ratio was thus 0.68, corresponding to a molar ratio of 19. The reactor was closed, stirred (300 rpm) and heated to 210° C. using a magnetic heating stirrer. The temperature of the reaction medium stabilized at 210° C.

after heating for 42 minutes. The pressure was the autogenous pressure of the alcohol at the operating temperature. The reaction was monitored once the temperature of the reaction medium had reached the set value. Samples were taken at regular intervals to follow the progress of the reaction in the reactor. After 6 h of reaction, stirring was stopped and the reactor was allowed to cool to ambient temperature. The samples which had been removed were washed with an aqueous saturated NaCl solution then after decanting, the upper organic phase was analyzed by gel permeation chromatography (GPC). The table below summarizes the results obtained.

|  | Samples (h) | $0^b$ | 2 | 4 | 6 |
|---|---|---|---|---|---|
| % by weight in organic phase$^a$ | Triglycerides | 40 | 20 | 5 | 1 |
|  | Diglycerides$^c$ | 12 | 8 | 3 | 2 |
|  | Monoglyceride | 5 | 8 | 5 | 3 |
|  | Vegetable oil methyl esters | 43 | 64 | 87 | 94 |

$^a$determined by GPC
$^b$t = 0 when the reaction medium reached the desired temperature
$^c$% representing diglycerides and sterols.

Note that the conversion of triglycerides had commenced even though the reaction medium had not reached 210° C. (43% of esters at t0).

At the end of the first step of the reaction, decanting was carried out by evaporating off the excess methanol and cooling the organic phase comprising the vegetable oil methyl esters. Said organic phase (25 g), containing 94% of esters, 3% of monoglycerides, 2% of diglycerides and 1% of triglycerides was introduced into a closed reactor, in the presence of 17 g of methanol and 1 g of catalyst C1 in order to obtain a biodiesel to specifications. The reactor was then closed, stirred (300 rpm) and heated to 210° C. with the aid of a heated magnetic stirrer. The temperature of the reaction medium stabilized at 210° C. after heating for 42 minutes. Samples were taken at regular intervals to follow the progress of the reaction in the reactor. After 6 h of reaction, stirring was stopped and the reactor was allowed to cool to ambient temperature. The samples which were removed were washed with an aqueous saturated NaCl solution then after decanting, the upper organic phase was analyzed by gel permeation chromatography (GPC). The table below summarizes the results obtained.

|  | Samples (h) | $0^b$ | 2 | 4 | 6 |
|---|---|---|---|---|---|
| % by weight in organic phase$^a$ | Triglycerides | 1 | 0.4 | 0.2 | 0.1 |
|  | Diglycerides$^c$ | 2 | 1 | 0.5 | 0.1 |
|  | Monoglyceride | 3 | 1 | 0.8 | 0.5 |
|  | Vegetable oil methyl esters | 94 | 97.6 | 98.5 | 99.3 |

$^a$determined by GPC
$^b$t = 0 when the reaction medium reached the desired temperature
$^c$% representing diglycerides and sterols.

The biofuel obtained satisfied the current regulations regarding the contents of tri-, di- and mono-glycerides as well as the ester content.

Example 8

Transesterification of Vegetable Oils (Rapeseed Oil) by Methanol in the Presence of Catalyst C2 (in Accordance with the Invention)

This example employed a batch transesterification process in a closed reactor. The oil used was rapeseed oil with the same characteristics and composition as used in Example 7.

25 g of rapeseed oil, 20 g of methanol and 1 g of catalyst C2 were introduced into a closed reactor at ambient temperature. The methanol/oil weight ratio was thus 0.8, corresponding to a molar ratio of 22. The reactor was closed, stirred (500 rpm) and heated to 160° C. using a magnetic heating stirrer. The temperature of the reaction medium stabilized at 160° C. after heating for 20 minutes. The pressure was the autogenous pressure of the alcohol at the operating temperature. The reaction was monitored once the temperature of the reaction medium had reached the set value. Samples were taken at regular intervals to follow the progress of the reaction in the reactor. After 5 h of reaction, stirring was stopped and the reactor was allowed to cool to ambient temperature. The samples which were removed were washed with an aqueous saturated NaCl solution then after decanting, the upper organic phase was analyzed by gel permeation chromatography (GPC). The table below summarizes the results obtained.

|  | Samples (h) | $0^b$ | 1 | 3 | 5 |
|---|---|---|---|---|---|
| % by weight in organic phase$^a$ | Triglycerides | 70 | 20 | 5 | 1 |
|  | Diglycerides$^c$ | 5 | 12 | 6 | 2 |
|  | Monoglyceride | 2 | 8 | 10 | 4 |
|  | Vegetable oil methyl esters | 23 | 60 | 79 | 93 |

$^a$determined by GPC
$^b$t = 0 when the reaction medium reached the desired temperature
$^c$% representing diglycerides and sterols.

Conversion of triglycerides had commenced even though the reaction medium had not reached 160° C. (23% of esters at t0).

At the end of the first step of the reaction, decanting was carried out by evaporating off the excess methanol and cooling the organic phase comprising the vegetable oil methyl esters. Said organic phase (25 g), containing 93% of esters, 4% of monoglycerides, 2% of diglycerides and 1% of triglycerides, was introduced into a closed reactor, in the presence of 20 g of methanol and 1 g of catalyst C2, in order to obtain a biodiesel to specifications. The reactor was then closed, stirred (300 rpm) and heated to 170° C. with the aid of a heated magnetic stirrer. The temperature of the reaction medium stabilized at 170° C. after heating for 30 minutes. Samples were taken at regular intervals to follow the progress of the reaction in the reactor. After 4 h of reaction, stirring was stopped and the reactor was allowed to cool to ambient temperature. The samples which were removed were washed with an aqueous saturated NaCl solution then after decanting, the upper organic phase was analyzed by gel permeation chromatography (GPC). The table below summarizes the results obtained.

|  | Samples (h) | $0^b$ | 1 | 2 | 4 |
|---|---|---|---|---|---|
| % by weight in organic phase$^a$ | Triglycerides | 1 | 0.5 | 0.2 | 0.1 |
|  | Diglycerides$^c$ | 2 | 0.8 | 0.2 | 0.1 |
|  | Monoglyceride | 4 | 2 | 1 | 0.6 |
|  | Vegetable oil methyl esters | 93 | 96.7 | 98.6 | 99.2 |

$^a$determined by GPC
$^b$t = 0 when the reaction medium reached the desired temperature
$^c$% representing diglycerides and sterols.

The biofuel obtained satisfied the current regulations regarding the contents of tri-, di- and mono-glycerides, as well as the ester content.

Example 9

Dehydration of Alcohols at Atmospheric Pressure in the Presence of Catalyst C3 (in Accordance with the Invention)

In this example, two different catalytic tests were carried out: the first was carried out with a feed constituted by ethanol and the second with a feed constituted by pentanol.

For each of the tests, a fixed traversed bed pilot unit was loaded with 1.5 g of catalyst C3. Before carrying out each of the tests, catalyst C3 was activated by calcining it at 550° C. in air for 2 h.

To carry out each of the tests, the ethanol or respectively pentanol was diluted with nitrogen so that the $N_2$/alcohol molar ratio was equal to 4. The feed diluted with nitrogen was injected onto the catalyst C3 placed in the traversed fixed bed reactor. The operating conditions for each of the tests are given in Table 3. Each test was carried out at atmospheric pressure (0.1 MPa). At the outlet from the reactor, the gas phase comprising nitrogen was separated from the organic liquid phase (if it exists) and from the aqueous liquid phase. In the case of the first catalytic test where the feed contained ethanol, the olefin produced was ethylene which was found in the gas phase and in the case of the second catalytic test where the feed contained pentanol, the olefins produced were pentenes which were found in the organic liquid phase. In addition to the operating conditions, Table 3 indicates the degree of conversion of the alcohol introduced as well as the olefins yield.

TABLE 3

Operating conditions and performances of catalyst C3 in the dehydration of alcohols at atmospheric pressure

| | Alcohol present in the feed | |
|---|---|---|
| Operating conditions | Ethanol | Pentanol |
| T (° C.) | 250° C. | 200° C. |
| HSV ($h^{-1}$) | 2 | 10 |
| TOS* (h) | 24 | 24 |
| Conversion (%) | 99.7 | 100 |
| Olefins yield (%) | 58 | 78.5 |

*TOS (time on stream) represents the contact time of the catalyst with the feed.
The conversion and yield were calculated as follows:
Conversion = (mass flow rate of alcohol$_{inlet}$ − mass flow rate of alcohol$_{outlet}$)/mass flow rate of alcohol$_{inlet}$.
Yield = (mass flow rate of olefin$_{outlet}$)/mass flow rate of alcohol$_{inlet}$.

These results demonstrate that catalyst C3 of the invention is very active in the transformation of alcohols to olefin(s) which are produced in optimal yield.

Example 10

Dehydration of Alcohols Under Pressure in the Presence of Catalyst C3 (in Accordance with the Invention)

In this example, two different catalytic tests were carried out: the first was carried out with a feed constituted by ethanol and the second with a feed constituted by pentanol.

For each of the tests, a fixed traversed bed pilot unit was loaded with 1.5 g of catalyst C3. Before carrying out each of the tests, catalyst C3 was activated by calcining it at 550° C. in air for 2 h.

To carry out each of the tests, the ethanol or respectively pentanol was diluted with nitrogen so that the $N_2$/alcohol molar ratio was equal to 4. The nitrogen-diluted feed was injected onto the catalyst C3 placed in the traversed fixed bed reactor. The operating conditions for each of the tests are given in Table 4. At the outlet from the reactor, the gas phase was separated from the organic liquid phase and from the aqueous liquid phase. In addition to the experimental conditions, Table 4 indicates the mass balance for the organic products recovered. These are divided into three categories: gases, liquids with low boiling points (bp<150° C.) and liquids with high boiling points (bp>150° C.).

TABLE 4

Operating conditions and performances of catalyst C3 in the dehydration of alcohols at atmospheric pressure

| Alcohol present in the feed | Ethanol | Pentanol |
|---|---|---|
| Operating conditions | | |
| T (° C.) | 330 | 300 |
| P (MPa) | 3 | 3 |
| HSV ($h^{-1}$) | 1.2 | 1.5 |
| TOS* (h) | 5 | 5 |
| Conversion (%) | 100 | 99.8 |
| Distribution of products in outlet effluent (% by weight) | | |
| Gas | 28.1% | 13.2% |
| Liquid (bp* <150° C.) | 34.6% | 29.8% |
| Liquid (bp* >150° C.) | 37.3% | 57% |

*bp: boiling point.

The conversion and yield were calculated in the manner described for Example 9.

The results shown in Table 4 demonstrate that the catalyst C3 of the invention is very active in the transformation of alcohols under pressure and produces products that can readily be incorporated into the gasoline pool (liquid phase with a boiling point of less than 150° C.) and into the diesel pool (liquid phase with a boiling point of more than 150° C.).

Example 11

Catalytic Evaluation of Catalyst C3 in an Oligomerization Process (in Accordance with the Invention)

An olefinic C4 cut derived from a catalytic cracking unit was dried over a type 13X molecular sieve to eliminate traces of sulphur and water. The composition of the feed at the end of these treatments was as follows:

| Composition of feed (wt %) | |
|---|---|
| Isobutane | 29.3 |
| n-butane | 8.8 |
| Isobutene | 18.3 |
| 1-butene | 13.9 |
| Σ2-butenes | 29.7 |

Catalyst C3 in accordance with the invention was loaded into a fixed bed reactor and tested in a reaction for the oligomerization of the feed described above.

The operating conditions applied in the oligomerization reactor were such that the pressure was 5.5 MPa and the HSV (volume flow rate of feed/catalyst volume) was equal to 1 $h^{-1}$. The catalyst was tested at two temperatures: initially at 200° C. then at 230° C.

The conversions of the olefins by the catalyst C3 at the oligomerization temperatures of 200° C. and 230° C. which were studied, and more particularly the conversions of isobutene and n-butenes, namely 1-butene and 2-butenes, are shown in Table 5. The conversion is defined as the ratio between the quantity of olefins converted and the total quantity of olefins initially present in the feed.

The catalyst C3 is a highly active catalyst in the reaction for the oligomerization of an olefinic feed. At 200° C. and 230° C., the conversion of the isobutene of the feed was complete (100%). The conversion of butenes, equivalent to the conversion of normal butenes and isobutene, was high and improved by increasing the temperature.

TABLE 5

Performance of catalyst C3 in the oligomerization of an olefinic C4 cut

| Temperature | 200° C. | 230° C. |
|---|---|---|
| Butene conversion (wt %) | 78.6 | 89.2 |
| Isobutene conversion (wt %) | 100 | 100 |

Example 12

Production of Linear Alkylbenzenes in the Presence of Catalyst C1 (in Accordance with the Invention)

50 cm³ of catalyst C1, which comprised a IZM-2 zeolite in the hydrogen form, was placed in a reaction zone supplied with a feed constituted by 72% by weight of benzene and 28% by weight of dodecene-1. The operating conditions for the alkylation of benzene by the dodecene-1 were as follows:
temperature: 135° C.;
pressure: 4 MPa;
HSV=1 h$^{-1}$ (cm³ benzene+dodecene-1 feed per cm³ of catalyst per hour);
benzene/dodecene-1 molar ratio: 30.

The catalytic performances are reported in Table 6 which shows the number of hours of operation at a conversion of more than 95% and the linearity of the alkylbenzenes formed.

TABLE 6

Catalytic performances of catalyst C1 in the alkylation of benzene

| | C1 |
|---|---|
| Number of hours/conversion >95% | 35 |
| Linearity of alkylbenzenes (%) | 91.8 |

The conversion measures the degree of transformation of the dodecene-1.

Conversion=(quantity of dodecene-1$_{inlet}$−quantity of dodecene-1$_{outlet}$)/quantity of dodecene-1$_{inlet}$.

The catalyst C1 in accordance with the invention is particularly active when it is used to carry out a process for the production of linear alkylbenzenes. It favours the production of linear alkylbenzenes.

Example 13

Process for Disproportionation of Toluene in the Presence of Catalyst C1 (in Accordance with the Invention)

Catalyst C1 which comprised an IZM-2 zeolite in the hydrogen form was introduced into a reaction zone where it was initially reduced in hydrogen at 450° C. for 2 h. Next, a feed constituted by 100% by weight of toluene was introduced into said zone.

The operating conditions for the disproportionation of toluene were as follows:
temperature: 400° C.;
total pressure: 2.5 MPa;
H$_2$/HC=8.5 mol/mol;
WHSV=4 h$^{-1}$ (mass of feed per gram of catalyst per hour).

The catalytic performances of the catalyst C1 are recorded in Table 7.

TABLE 7

Catalytic performances of catalyst C1 for the disproportionation of toluene

| Overall conversion (%) | 49.7 |
|---|---|
| Yields (% by weight) | |
| Light (C1-C4) | 2.5 |
| Benzene | 22.2 |
| Xylenes | 21.1 |
| Ethylbenzene | 0.8 |
| Heavy | 3.1 |

Catalyst C1 was active in carrying out the toluene disproportionation process. Benzene and xylene were produced in satisfactory yields.

The invention claimed is:

1. A catalyst comprising at least one IZM-2 zeolite and at least one matrix, said zeolite having an X ray diffraction diagram including at least the peaks recorded in the table below:

| 2 theta (°) | d$_{hkl}$ (Å) | I$_{rel}$ |
|---|---|---|
| 5.07 | 17.43 | Vw |
| 7.36 | 12.01 | Vs |
| 7.67 | 11.52 | Vs |
| 8.78 | 10.07 | S |
| 10.02 | 8.82 | Vw |
| 12.13 | 7.29 | Vw |
| 14.76 | 6.00 | Vw |
| 15.31 | 5.78 | Vw |
| 15.62 | 5.67 | Vw |
| 16.03 | 5.52 | Vw |
| 17.60 | 5.03 | Vw |
| 18.22 | 4.87 | Vw |
| 19.01 | 4.66 | Vw |
| 19.52 | 4.54 | Vw |
| 21.29 | 4.17 | M |
| 22.44 | 3.96 | W |
| 23.10 | 3.85 | Mw |
| 23.57 | 3.77 | W |
| 24.65 | 3.61 | Vw |
| 26.78 | 3.33 | W |
| 29.33 | 3.04 | Vw |
| 33.06 | 2.71 | Vw |
| 36.82 | 2.44 | Vw |
| 44.54 | 2.03 | Vw | in which: Vs = very strong; S = strong; M = medium; Mw = medium weak; W = weak; Vw = very weak, and having a chemical composition expressed, as the anhydrous base in terms of moles of oxides, by the following general formula: XO$_2$: aY$_2$O$_3$: bM$_n$O, in which X represents at least one tetravalent element, Y represents at least one trivalent element and M is at least one alkali metal and/or alkaline-earth metal, a and b respectively representing the number of moles of Y$_2$O$_3$ and M$_n$O; and a is in the range 0.001 to 0.5, b is in the range 0 to 1 and n is in the range 1 to 2.

2. A catalyst according to claim 1, in which X is silicon and Y is aluminium.

3. A catalyst according to claim 1, in which said zeolite is in the protonated form.

4. A catalyst according to claim 1, in which said zeolite is in its basic form.

5. A catalyst according to claim 1, in which said matrix contains alumina.

6. A catalyst according to claim 1, in which it comprises at least one additional metal selected from metals from groups IIIb, IVa and IVb.

7. A process for the production of at least one alcoholic ester from at least one compound belonging to the triglycerides family and at least one compound carrying an alcohol function carried out in the presence of at least one catalyst in accordance with claim 1.

8. A process according to claim 7, in which said catalyst comprises at least one IZM-2 zeolite in the hydrogen form or in the basic form.

9. A process for the transformation of at least one aliphatic compound containing 1 to 18 carbon atoms and carrying an alcohol function, said process being carried out in the presence of at least one catalyst according to claim 1.

10. A process according to claim 9, in which said transformation which takes place is a dehydration reaction during which said aliphatic compound carrying an alcohol function is dehydrated to olefin(s) with the production of water.

11. A process according to claim 9, in which said transformation which takes place simultaneously dehydrates said aliphatic compound to olefin(s) and oligomerizes said olefin(s) in the same reactor.

12. A process for oligomerizing an olefinic feed, consisting of bringing said feed into contact with at least one catalyst in accordance with claim 1.

13. A process for producing phenylalkanes, comprising a reaction for alkylation of at least one aromatic compound by at least one linear olefin, said process being carried out in the presence of at least one catalyst in accordance with claim 1.

14. A process according to claim 13, in which said aromatic compound is benzene and said linear olefin contains 9 to 16 carbon atoms per molecule.

15. A process for the disproportionation of toluene to produce benzene and xylenes carried out in the presence of at least one catalyst according to claim 1.

16. A catalyst according to claim 2, in which said zeolite is in the protonated form.

17. A catalyst according to claim 2, in which said zeolite is in its basic form.

18. A catalyst according to claim 2, in which it comprises at least one additional metal selected from metals from groups IIIb, IVa and IVb.

19. A catalyst according to claim 3, in which it comprises at least one additional metal selected from metals from groups IIIb, IVa and IVb.

20. A catalyst according to claim 4, in which it comprises at least one additional metal selected from metals from groups IIIb, IVa and IVb.

* * * * *